United States Patent [19]
Graulich et al.

[11] Patent Number: 6,103,527
[45] Date of Patent: Aug. 15, 2000

[54] PROMOTER OF THE HUMAN ENDOGLIN GENE

[75] Inventors: Wolff Graulich, Coelbe; Dirk Nettelbeck, Marburg; Hans-Harald Sedlacek, Marburg; Rolf Mueller, Marburg, all of Germany

[73] Assignee: He Hoechst Aktiengesellschaft, Germany

[21] Appl. No.: 09/019,689

[22] Filed: Feb. 6, 1998

[30] Foreign Application Priority Data

Feb. 6, 1997 [DE] Germany .............. 197 04 301

[51] Int. Cl.[7] ................................ C12N 5/10
[52] U.S. Cl. .............. 435/367; 435/320.1; 536/24.1
[58] Field of Search ................ 435/367, 320.1; 536/24.1

[56] References Cited

PUBLICATIONS

Bellón et al., *Eur. J. Immunol.*, vol. 23, pp. 2340–2345, 1993.

*Primary Examiner*—James Ketter
*Attorney, Agent, or Firm*—Foley & Lardner

[57] ABSTRACT

The promoter of the human endoglin gene, parts thereof, and compositions containing these are useful for high level control of gene expression, particularly in endothelial cells. The promoter, and promoter active portions of the promoter are shown to have unexpected activity and are particularly relevant for therapeutic use.

13 Claims, 7 Drawing Sheets

Figure 1 - (SEQ ID NO: 1)

```
1       CGGGGGTTCC  TCCTCTGTAA  AGTGGAGGTA
31      TAACGGTACC  CACCTCCTGG  GGTGGCTGTG
61      AGGATTCAGA  GCTGATAAGG  TGAACGCCTA
91      GGGCGGGCCC  TGGTGCAGAG  AGAGCGCTCA
121     GCTCCTAGGG  CTGGATTAAC  TGTCCCTGGG
151     GCACAGATCT  CGGTCTGGGG  CCTGTGGAAA
181     CCTCAGAGCC  ACCCTGAAC   CCCCACCGAG
211     CCACCCTTTG  CCTCGCAGTG  CCCATGGCCT
241     CGTCTCCGAG  GTTACAGGAA  AAGGCAGAGG
271     AGATGCCCTT  CTCAGGGTGG  CCCTCTGGGA
301     GAGGACACTC  TCCCTTGACC  TCAAAGCCAC
331     GCTTGGCTGC  AAACTGGCCA  GGCAGCCACA
361     AGGCTGGGCA  AGCAGAACGA  TCCCTAATCC
391     CCACCCAAAG  AGCCACACCG  ACCCTCCCAG
421     CCGCTGTGAC  AGCTCCTGCA  GAGACAAACA
451     CACGGCCTAC  TCTTGTCACC  CGGGCCGGCC
481     AATAAGCACG  GAGAGGCAAG  GCCTCAGACC
511     CTGGACAGAC  ATCCTCCCTC  CAGAGGCACC
541     AGGGCCTCAG  CCTTCTCCTC  CCTCCCTGGG
571     CCTCAATTTC  TCCACCTGTG  ACCCAGGGCA
601     GGTGGATCCA  GGGAGAAGAA  CCTTCTGGCT
631     CCATCTCACC  ATGGGTCCTG  CCAGCACACA
661     CAAAGATTTG  GCCTCTCAAA  GCCTAGCTCT
691     GCCAGCGTCC  TTCTGCTCAA  GAACTCTCCA
721     TGACTCCCAG  TGGCCCTAAG  GACAAAGTCC
751     TGGCATTTGA  GGCCCTCCCA  ATGCAGGGCC
781     AGACTCTGCC  TCTCCAGCTT  CCTGTCCCCA
811     CCACACCCCT  GCTGGTCTCA  CGGTGGTCCG
841     ACTGTTTCCT  GCTTCTGTGC  CTTTGCTTAG
871     TCTGGCACCC  CTGCCTGGCA  TGCTTTCCTC
901     ACCCCTTCTT  CTCCCCAATC  CCAACTCACC
931     CAGTCTTTCA  AAGGGCAGGC  CTAAATACCA
961     GGCCCTCCAG  GTGGCCCAGG  ATTCCTTCTC
991     TGAGCTTTCA  TGGGCCTGGC  CCTGGGTGCT
1021    ACCTGTGAGT  AGTCCCACGG  TGGGTACATA
1051    GTAGGTGCGC  TTACTGTTCG  CAGAATGAAC
1081    ATGGGACAGT  TTGGGGACTG  TCACCCAGCT
1111    CAGGGAGCAC  TGATGGGGAA  GCATCTCCTG
1141    TATGTCCCAG  GGCTCAGTGC  TGTAGTGTCC
1171    TGACCCTCAG  AAATCTCATA  ATGGCTTGGT
1201    CAGGAAGGCA  TCGTGCCCCA  CTTTGCAAAC
1231    AGGGGGTGCT  GAGAATTGAG  GGGCCTTGTC
1261    CAAGGTCTCA  TGGCTAGGAG  CAAGCAGAAT
1291    CGGATTTGAA  CCCAGGGCCA  CGTGACTTCA
1321    GAAGTGCCAT  TAAAGTCCCC  ATAATTCGGA
1351    GCTGTCTTCT  TTTTTTTTTT  CTTTCTTTTT
1381    TTTGAGACCG  AGCCTCACTC  TGTCACCTAG
1411    GCCAGGAGTG  CAGTGGTCTG  ATCTCAGCTC
1441    ACTGCAACCT  CCGCCTCCTA  GGTTCAAGTG
1471    ATTCTCTAGC  CTCAGCCTCC  CAAGTAGCTG
```

Figure 1 cont.

```
1501      GGACTACAGG   CGCACGTCAT   CATGCCCAGC
1531      TAACTTTTGT   ATTTTTAGTA   GAGATGGGTT
1561      TTCACCATGT   TGGTCAGGCT   GGTCTCGAAC
1591      TCCTGACCTC   AAGTGATCCG   TCTGCCTCGG
1621      CCTCTCAAAG   TGCTGGGATT   ATAGGCTTGA
1651      GCCACTACAC   TCGGCCTGGA   GCTGTGTTTT
1681      GTCGGTGAAG   GATTTTCCAC   CCATGAAGGG
1711      GTCAGACGTG   AAGCGTGTGG   CCCTGGGCAG
1741      CTCCTCTGAG   CCCAGAGACG   CCAGCCCTAG
1771      CCGCCTTGCT   GTGCCACTTT   GGGACTTCCC
1801      TCCCTAGCCT   GAGCTTCAGT   TTTCCTGCCT
1831      GTTAGGCAGC   CCCATGTCAA   CTGCACTTAG
1861      TAGGCCGGGT   TTGATGCCCG   ACAAGACGTG
1891      AAGTGGTGGA   GGTGGGCAGG   ATCCCAGCGC
1921      TACCATCTTC   TTGAACCAGT   GATCTCAACA
1951      CATCGGATTT   CTGTTTCCTC   ATCTGCAAAA
1981      TGGGATCAGT   GAGCTCAGGT   GGGTCACAAA
2011      TTCTACAGGA   ACTACTTTAG   CCAAGCCCGG
2041      CCCCCTGAAA   GTTCCCCTCG   GTGGGCAGTT
2071      AGGGTGATTG   TTTTCATCTG   TGGGGCTCCC
2101      TGATGCGTCC   CACCCACCAG   CCTTGGAGAG
2131      GGTGGGATGG   GAGGGTGGGG   TGCTTGGGGA
2161      GACAAGCCTA   GAGCCTGGGC   CCTCCCACCC
2191      CACTGCCTCC   CCCCATCCCA   GGGCCCCCCA
2221      CCCAGTGACA   AAGCCCGTGG   CACTTCCTCT
2251      ACCCGGTTGG   CAGGCGGCCT   GGCCCAGCCC
2281      CTTCTCTAAG   GAAGCGCATT   TCCTGCCTCC
2311      CTGGGCCGGC   CGGGCTGGAT   GAGCCGGGAG
2341      CTCCCTGCTG   CCGGTCATAC   CACAGCCTTC
2371      ATCTGCGCCC   TGGGGCCAGG   ACTGCTGCTG
2401      TCACTGCCAT   CCATT
```

Figure 2

| Nucleotide Sequence | Relative Activity |
|---|---|
| SV40 promoter | 1 |
| endoglin promoter (SEQ ID NO: 1) 1-2415 | 11.5 |
| Partial Sequences (SEQ ID NO: 1) | |
| 36-2415 | 10.2 |
| 470-2415 | 13.0 |
| 948-2415 | 10.0 |
| 1310-2415 | 2.0 |
| 1847-2415 | 3.3 |
| 2339-2415 | 0.2 |

Promoter activity of the cloned hendoglin 5' region

FIG. 6

PROMOTER OF THE HUMAN ENDOGLIN GENE

FIELD OF THE INVENTION

The present invention relates generally to promoters that have high activity and specifically to controlling elements for human endoglin gene expression in endothelial cells. The invention further relates to the use of such moieties in preparing therapeutic agents.

BACKGROUND OF THE INVENTION

An important problem in gene therapy is the control of the transcription and translation of an effector gene which is inserted into the cell. At the level of transcription, this control is made possible by adding on a promoter or enhancer sequence upstream of the coding sequence of the effector gene. The "promoter sequence" is understood as being a gene segment to which regulatory proteins, the so-called transcription factors, which in their totality activate the transcription of the downstream effector gene, are able to bind. Those regions which lie in the direction of transcription are designated "downstream" sequences, whereas sequences which are arranged in the opposite direction are designated "upstream" sequences. An "effector gene" is generally understood as being a structural gene whose gene product has, for example, a desirable effect in the gene therapy sense.

Such promoter or enhancer sequences can be non-cell-specific, cell-specific, virus-specific, metabolism specific or cell cycle-specific. Examples of these promoter sequences and their use, e.g. for the gene therapy of different diseases, are listed in Patent Applications WO 96/06940, WO 96/06938, WO 96/06941 and WO 96/06939. In addition, these patent applications present techniques and examples for combining these promoter sequences, e.g. for the purpose of controlling an effector gene cell-specifically and cell cycle-specifically.

Depending on the choice and combinations of the promoters, these promoters bring about a more or less restricted and/or more or less powerful transcription of the effector gene.

The endothelial cell is an example of an advantageous target cell for gene therapy, on the one hand because endothelial cells are directly accessible to gene constructs which are injected into the circulatory system and, on the other hand, because they are directly involved in the development and progress of a number of disorders, such as tumor diseases, inflammations, allergies, autoimmune diseases, organ rejection reactions and circulatory and coagulation disorders, and also in healing processes, and/or are directly adjacent to the site of these disorders.

As a rule, target cell-specific promoters are promoters of genes for those proteins which are formed particularly vigorously, or to a large extent exclusively, in the relevant target cell. In the case of the endothelial cell, endoglin is an example of one of these proteins.

Endoglin is a non-signal-transferring receptor of TGFP (Gougos et al., J. Biol. Chem. 265, 8361 (1990), Cheifetz, J. Biol. Chem. 267, 19027 (1992), Moren et al., BBRC 189, 356 (1992)). While it occurs in small quantities on normal endothelium, it is expressed to an increased extent on proliferating endothelium (Westphal et al., J. Invest. Derm. 100, 27 (1993), Burrows et al., Pharmac. Ther. 65, 155 (1994). No further information is available with regard to promoter strength and cell specificity. Despite the fact that the endoglin gene has been known for about 4 years (Bellon et al., (1993), it has not so far been possible to isolate the endoglin promoter.

The cDNA sequence for human endoglin has been described by Bellon et al. (Eur. J., Immunol. 23, 2340 (1993)), while that for murine endoglin has been described by Ge et al. (Gene 138, 201 (1994)). While sequence information is available for a part of the 5'-non-translated region of the endoglin gene, nothing is known about the function of this region or about the promoter region.

The VEGF receptor is another endothelial cell-specific protein. In this case, two receptors are distinguished (Plate et al., Int. J. Cancer 59, 520 (1994)): on the one hand, VEGF receptor 1 (flt-1), (de Vries et al., Science 255, 989 (1992)), which contains an fms-like tyrosine kinase in the cytoplasmic moiety, and VEGF receptor 2 (flk-1, KDR), (Terman et al., BBRC 187, 1579 (1992)), which contains a tyrosine kinase in the cytoplasmic moiety. Both receptors are found almost exclusively on endothelial cells (Senger et al., Cancer Metast. Rev. 12, 303 (1993)).

Other endothelial cell-specific receptor tyrosine kinases are tie-1 or tie-2 (Partanen et al., Mol. Cell. Biol. 12, 1698 (1992), Schnurch und Risau, Development 119, 957 (1993), Dumont et al., Oncogene 7, 1471 (1992)), and the B61 receptor (Eck receptor), (Bartley et al., Nature 368, 558 (1994), Pandey et al., Science 268, 567 (1995), van der Geer et al., Ann. Rev. Cell. Biol. 10, 251 (1994)).

Other endothelial cell-specific proteins are the B61 molecule, which represents the ligand for the B61 receptor (Holzman et al., J. Am. Soc. Nephrol. 4, 466 (1993), Bartley et al., Nature 368, 558 (1994)), endothelin, in particular endothelin B (O'Reilly et al., J. Cardiovasc. Pharm. 22, 18 (1993), Benafti et al., J. Clin Invest 91, 1149 (1993), O'Reilly et al., BBRC 193, 834 (1993)), whose promoter sequence has been described by Benafti et al., J. Clin. Invest. 91, 1149 (1993), endothelin 1 (Yanasigawa et al., Nature 332, 411 (1988)), whose promoter sequence has been described by Wilson et al., Mol. Cell. Biol. 10, 4654 (1990), endothelin receptors, in particular the endothelin B receptor (Webb et al., Mol. Pharmacol. 47, 730 (1995), Haendler et al. J. Cardiovasc. Pharm. 20, 1 (1992)), mannose 6-phosphate receptors (Perales et al., Eur. J. Biochem. 226, 225 (1994)), whose promoter sequences have been described by Ludwig et al. (Gene 142, 311 (1994), Oshima et al., (J. Biol. Chem. 263, 2553 (1988)) and Pohlmann et al. (PNAS USA 84, 5575 (1987)), and von Willebrand factor (vWF), whose promoter sequence has been described by Jahroudi and Lynch (Mol. Cell. Biol. 14, 999 (1994)), Ferreira et al. (Biochem. J. 293, 641 (1993)) and Aird et al. (PNAS USA 92, 4567 (1995)).

Other endothelial cell-specific proteins are IL-1 in the form, for example, of IL-1(x and IL-1p, which are produced by activated endothelial cells (Warner et al., J. Immunol. 139, 1911 (1987)) and whose promoter sequences have been described by Hangen et al., Mol. Carcinog. 2, 68 (1986), Turner et al., J. Immunol. 143, 3556 (1989), Fenton et al., J. Immunol. 138, 3972 (1 987), Bensi et al., Cell Growth Diff. 1, 491 (1990), Hiscoft et al., Mol. Cell. Biol. 13, 6231 (1993) and Mori et al., Blood 84, 1688 (1994), IL-1 receptor, whose promoter sequence has been described by Ye et al., PNAS USA 90, 2295 (1993), and vascular cell adhesion molecule (VCAM-1), with the expression of VCAM-1 in endothelial cells being activated by lipopolysaccharides, TNF-(X (Neish et al., Mol. Cell. Biol. 15, 2558 /1995)), IL-4 (Iademarco et al., J. Clin. Invest. 95, 264 (1995)) and IL-5 (Marni et al., J. Clin. Invest. 92, 1866 (1993)). The promoter sequence of VCAM-1 has been described by Neish et al., Mol. Cell. Biol. 15, 2558 (1995), Ahmad et al., J. Biol. Chem. 270, 8976 (1995), Neish et al., J. Exp. Med. 176, 1583 (1992), Lademareo et al., J. Biol.

Chem. 267, 16323 (1992), and Cybuisky et al., PNAS USA 88, 7859 (1991).

Other endothelial cell-specific promoters are synthetic activator sequences, in that synthetic activator sequences, which are composed of oligomerized binding sites for transcription factors which are preferentially or selectively active in endothelial cells, for example the transcription factor GATA-2, whose binding site in the endothelin I gene is 5'-TTATCT-3' (Lee et al., Biol. Chem. 266, 16188 (1991), Dorfmann et al., J. Biol. Chem. 267, 1279 (1992) and Wilson et al., Mol. Cell. Biol. 10, 4854 (1 990)), can also be used as an alternative to natural endothelium-specific promoters, and the brain-specific, endothelial glucose-1 -transporter, in that brain endothelial cells characteristically express this transporter very strongly in order to effect transendothelial transport of D-glucose into the brain (Gerhart et al., J. Neurosci. Res. 22, 464 (1989)). The promoter sequence has been described by Murakami et al. (J. Biol. Chem. 267, 9300 (1992)).

While being fairly specific for endothelial cells, some of these promoters, for example the promoter for the gene for von Willebrand factor or for the gene for VEGF receptor 1 (flk-1), are, however, only of relatively low activity. While the activity of such "weak" promoters can be increased by combining them with a basal promoter (e.g. SV40) or an enhancer, this then usually leads to an accompanying decrease in specificity. Accordingly, strong promoters are needed for high expression of transgenic materials in endothelial cells.

SUMMARY OF THE INVENTION

The object of the present invention is, therefore, to provide a promoter that causes high gene expression. Another object is to provide a promoter that can be used for selective transgenic expression in endothelial tissue.

In carrying out these aims, the inventors provide a promoter of the human endoglin gene, comprising SEQ ID NO: 1, functional moieties of this gene, and variants thereof. Various embodiments provide, nucleic acid constructs and vectors that contain such sequences, their functional moieties and variants.

One embodiment of the invention is drawn to a promoter of the human endoglin gene, comprising a sequence selected from SEQ ID NO: 1 or a variant sequence thereof. Another embodiment is drawn to a vector comprising a promoter of the human endoglin gene, said promoter having a sequence that comprises SEQ ID NO: 1, a functional moiety, or a variant sequence thereof. In yet another embodiment the invention pertains to a pharmaceutical composition for treating a disease, said composition comprising a sequence of SEQ ID NO: 1, a functional moiety, or a variant sequence thereof. Other embodiments will be apparent from this specification and also recognized by skilled workers in this field.

DETAILED DESCRIPTION OF THE PREFERRED EMBODIMENTS

Figure 1:
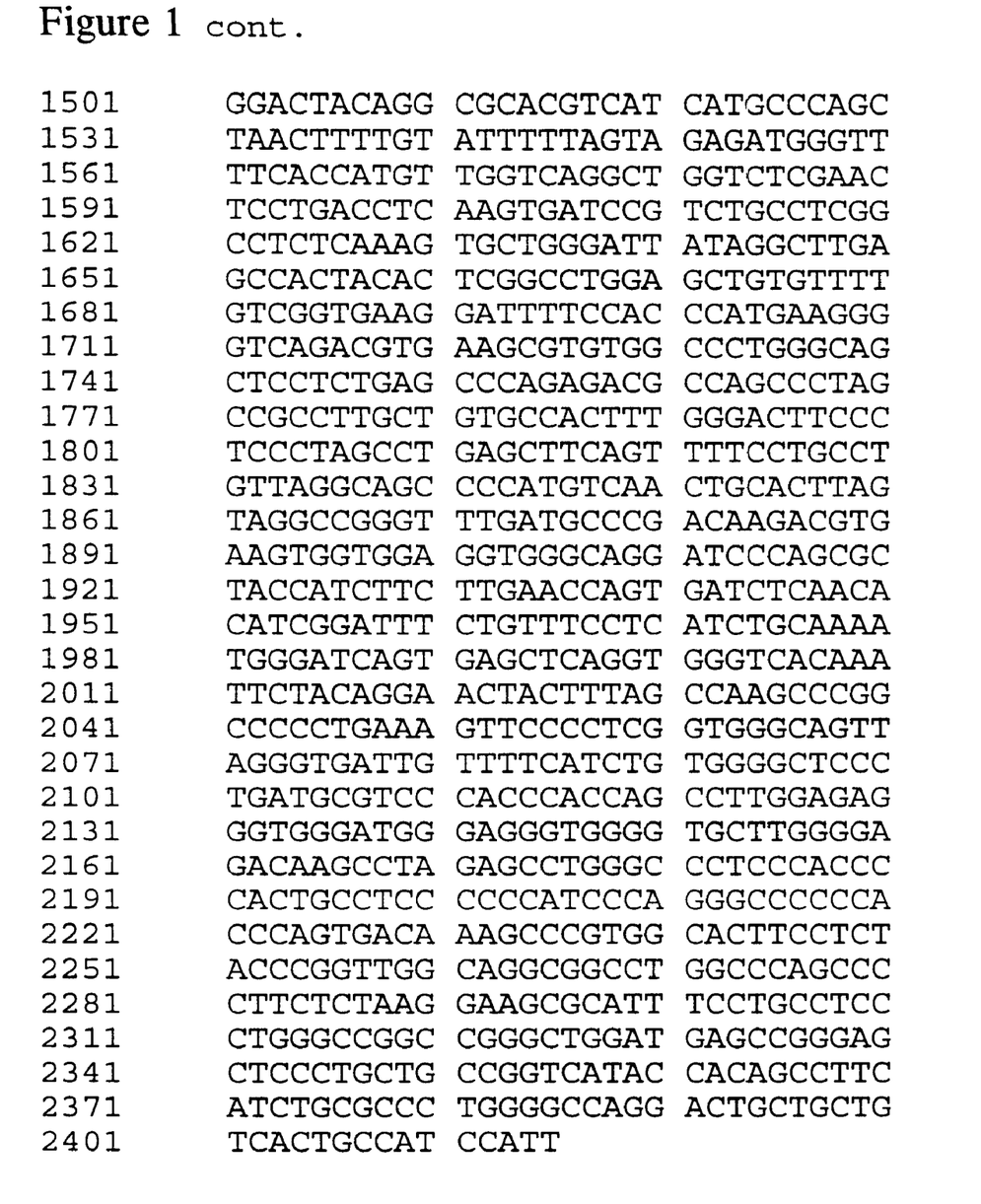
FIG. 1 (SEQ ID NO: 1) shows the sequence of the human endoglin promoter. Base pair 1 corresponds to the region of the sequence which is located farthest 5'. A highly conserved Alu sequence is located in the region of base pairs 1360–1666, while the homology with the documented *M. musculus* cDNA begins in the 3' region at base pair 2300, and the documented part of the *H. sapiens* cDNA (5'-untranslated region) begins at base pair 2379.

The inventors surprisingly found the endoglin gene promoter to be both strong and endothelium specific. Moreover, this promoter, and functional moieties and variants of it, exhibit these properties more strongly than expected, based on studies of another endothelial cell promoter. The inventors discovered that the endoglin promoter extends over a maximum of 2415 base pairs (see FIG. 1, SEQ ID NO: 1), preferably encompasses the nucleotide sequence 12378, and includes an RNA transcription initiation sequence.

The inventors found that the entire promoter sequence displays these advantageous properties, but also that parts of the promoter sequence display strong endothelial cell-specific activity. These portions were individually tested in endothelial cells and compared with the SV40 promoter as a standard, as described below.

Figure 2:
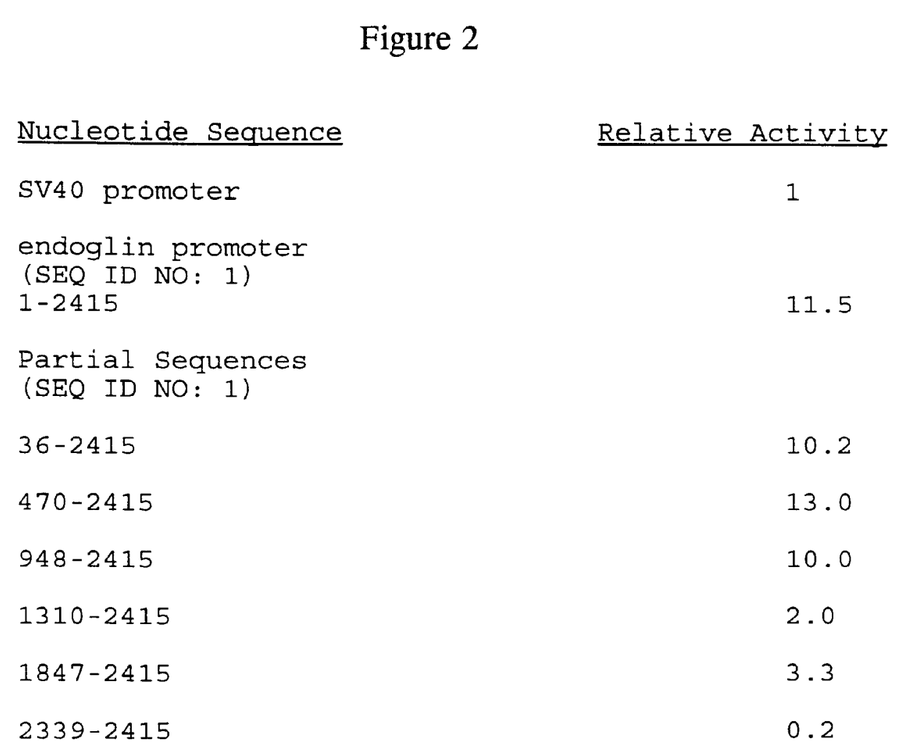
FIG. 2 shows the relative activities of 5' terminally deleted constructs of the endoglin promoter.

A comparison of regulatory element activities with that of the SV40 promoter was made using endothelial cells. FIG. 2 shows these relative activities for 5' terminally deleted constructs of the endoglin gene promoter.

In order to characterize the promoter according to the invention, the promoter sequence of the endoglin gene, or parts thereof, were linked to a reporter gene (e.g. the gene encoding the enzyme luciferase) in the plasmid pGL3 (Promega), and endothelial cells (ECV-304 cell line). For comparison, cervical carcinoma cells (HeLa cell line) were transfected with this construct. Surprisingly, it was found that the endoglin promoter is about 80 times as strong as the vWF promoter. This is surprising because vWF is, as mentioned above, expressed in an endothelium specific manner and it would consequently have been expected that the strength of the endoglin promoter would be similar to that of the vWF promoter.

It was also found that the endoglin promoter is about 30 times more active in endothelial cells than in cervical carcinoma cells. This is surprising because the vWF promoter, which is likewise endothelium-specific, has a similar strength in cervical carcinoma cells and in endothelial cells. Consequently, the vWF gene promoter is distinctly surpassed by the endoglin promoter, according to the invention, both with regard to its strength and with regard to its endothelium specificity.

For purposes of the invention, "functional moieties of the promoter" means all partial sequences of the promoter which possess promoter activity. Advantageous sequences in this context are the partial sequences from approximately 1 to approximately 2378, from approximately 36 to approximately 2378, from approximately 470 to approximately 2378 and from approximately 948 to approximately 2378, and also the partial sequences from approximately 36 to approximately 2415, from approximately 470 to approximately 2415 and from approximately 948 to approximately 2415, preferably the partial sequences from approximately 470 to approximately 2415 and from approximately 470 to approximately 2378. Partial sequences possessing promoter activity also extend, for example, from approximately 1310 to approximately 2415 and from approximately 1310 to approximately 2378, and from approximately 1847 to approximately 2415 and from approximately 1847 to approximately 2378.

The phrase "sequence selected from SEQ ID NO: 1" includes not only the entire sequence, but portions of this sequence that have promoter activity. This definition includes functional moieties of the promoter.

The present invention is not restricted to sequences selected from SEQ ID NO: 1 (i.e. the entire sequence, and functional moieties thereof) but also comprises variants which possess promoter activity. Variants of this nature comprise, for example, deletions, additions, insertions and/or substitutions of one or more bases, preferably of from approximately 1 to approximately 50, in particular of from approximately 1 to approximately 25, especially of from approximately 1 to approximately 5, bases from a sequence selected from SEQ ID NO: 1. Thus, a "variant" as termed here, is a modified sequence from SEQ ID NO: 1 that still has promoter activity. Modifications can be made by various techniques that are known to the skilled artisan. An example of such a technique is given in Sambrook, J. et al., MOLECULAR CLONING. LABORATORY MANUAL, Second Edition, Cold Spring Harbor Laboratory Press (1989).

The promoter activity can be readily measured, for example, using the luciferase assay described by Herber et al. (Oncogene 9, 1295 (1994)) and Lucibello et al. (EMBO J. 14, 132 (1995)). The present invention furthermore also relates to a nucleic acid construct which comprises a) at least one nucleic acid sequence of the promoter according to the invention (component a)) and, where appropriate, b) at least one effector gene (component b)), with the transcription of this effector gene being activated by component a). Component a) is preferably located upstream of component b).

The invention furthermore relates to a nucleic acid construct in which the promoter sequence of the endoglin gene according to the invention is combined with another target cell-specific, virus-specific, metabolism specific or cell cycle-specific promoter sequence and with at least one effector gene, in which this combination of promoter sequences controls the activation of at least one effector gene.

A nucleic acid construct according to the invention is preferably composed of DNA. The term "nucleic acid construct" is understood as meaning artificial structures which are composed of nucleic acid and which can be transcribed in the target cells. They are preferably inserted into a vector, for example into non-viral vectors, such as plasmids, or viral vectors. The skilled artisan is familiar with the preparation of non-viral vectors and of viral vectors. Such preparation is explained, for example, in Sambrook, J. et al., MOLECULAR CLONING. LABORATORY MANUAL, Second Edition, Cold Spring Harbor Laboratory Press (1989).

The present invention also relates to cells which harbor a nucleic acid construct according to the invention. Such cells can be prokaryotic or eukaryotic, and advantageously are endothelial cells and hematopoietic cells, such as CD34 positive stem cells, macrophages, or B-lymphocytes.

In general, the choice of an effector gene, in accordance with the invention, depends on the disease to be treated with the gene construct.

Examples of effector genes are those used for the therapy of tumor diseases, leukemias, autoimmune diseases, allergies, arthritis, inflammations, organ rejections, graft versus host reactions, diseases of the blood coagulation system, cardiovascular diseases, anemia, infections or damage to the CNS and are described in detail in Patent Applications WO 96/06940, WO 96/06938, WO 96/06941 and WO 96/06939.

For example, an effector gene in conformance with the present invention may encode a cytokine such as IL-1, IL-2, TL-4, IL-12, IL-3, or IL-5, a chemokine, a growth factor, a receptor for a cytokine, a receptor for a chemokine or a receptor for a growth factor, a cytokine antagonist, a protein which induces cytostasis, cytotoxicity or apoptosis, an antibody or an antibody fragment, an antiangiogenic protein, such as angiostatin, an interferon, such as IFNα, IFNβ or IFNγ, a coagulation factor, a coagulation inhibitor, a fibrinolytic protein, an enzyme which cleaves a precursor of a drug, thereby forming a drug, an enzyme such as bacterial nitroreductase, bacterial β-glucuronidase, plant β-glucuronidase derived from Secale cereale, human β-glucuronidase, human carboxypeptidase (CB), e.g. mast cell CB-A or pancreas CB-B, or bacterial carboxypeptidase, bacterial β-lactamase, bacterial cytosine deaminase, human catalase or peroxidase, phosphatase, in particular human alkaline phosphatase or human acid prostate phosphatase, type 5 acid phosphatase, oxidase, in particular human lysyl oxidase or human acid D-aminooxidase, peroxidase, in particular human glutathione peroxidase, human eosinophilic peroxidase or human thyroid peroxidase, a protein which exerts an effect on blood circulation such as kallikrein or endothelial cell nitric oxide synthase, or an antigen of an infectious pathogen which evokes an immune reaction. Particularly advantageous in this context is β-glucuronidase protein.

A nucleic acid construct according to the invention can furthermore comprise two or more identical or different eeffector genes which are linked to each other by way of promoter sequences or internal ribosomal entry sites (IRES). Examples of these are given in the above mentioned patent applications. Methods for preparing these constructs are well known to the skilled artisan, as for example, described in the above mentioned patent applications which are incorporated by reference in their entireties.

A nucleic acid construct according to the invention can be used, for example, to express a gene 1) specifically in an endothelial cell, 2) specifically in an endothelial cell and also in a metabolism specific manner, 3) specifically in an endothelial cell and also cell cycle-specifically and 4) specifically in an endothelial cell and virus-specifically (and optionally cell cycle or metabolic specific). The controlled gene preferably encodes a pharmacologically active compound or an enzyme which cleaves an inactive precursor of a drug, thereby forming an active drug.

Preference is given to using a nucleic acid construct according to the invention to prepare a pharmaceutical composition (drug), for treating at least one of the above mentioned diseases, with the preparation of a pharmaceutical generally comprising the cloning of the nucleic acid construct into a suitable vector, which is then, for example, administered to the patient. A skilled artisan is familiar with other ways of using a promoter and these other ways are possible according to the invention. A skilled artisan also will appreciate creation and modification of various nucleic acid constructs according to the invention.

The pharmaceutical compositions contemplated are intended for parenteral, topical, oral or local administration and generally comprise a pharmaceutically acceptable carrier and an amount of the active ingredient sufficient to reverse or prevent the bad effects of a disease state. The carrier may be any of those conventionally used and is limited only by chemico-physical considerations, such as solubility and lack of reactivity with the compound, and by the route of administration.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

The pharmaceutically acceptable carriers described herein, for example, vehicles, adjuvants, carriers or diluents, are well-known to those who are skilled in the art and are readily available to the public. It is preferred that the pharmaceutically acceptable carrier be one that is chemically inert to the active compounds and one that has no detrimental side effects or toxicity under the conditions of use.

EXAMPLE

The following example, together with the table and Figures described above, is intended to describe the invention in more detail without limiting it.

The PromoterFinder TM DNA Walking kit (Clontech) was used for cloning the promoter. Using this kit, an approximately 2.4 kilobase pair fragment located 5' of the documented sequence was amplified, in two PCR runs, from the 5'-untranslated region of human endoglin CDNA with the aid of the two gene-specific primers

E1: GCTGGGCTGGAGTTGCTGTCCGAAGGATG (SEQ ID NO: 2)

E2: AATGGATGGCAGTGACAGCAGCAGTCCTG (SEQ ID NO: 3).

The PCR conditions for this were as follows:

1. PCR: Primer E1, 25s at 94° C., 25s×94° C., 20s at 63° C., 4 min at 68° C., 39 cycles, 4 min at 68° C.

2. (nested) PCR: Primer E2, 25s at 94° C., 25s at 94° C., 20s at 61° C. 4 min at 68° C., 26 cycles, 4 min at 68° C.

Polymerase: Expand (TM) Long Template PCR system (Boehringer Mannheim)

Figure 3:
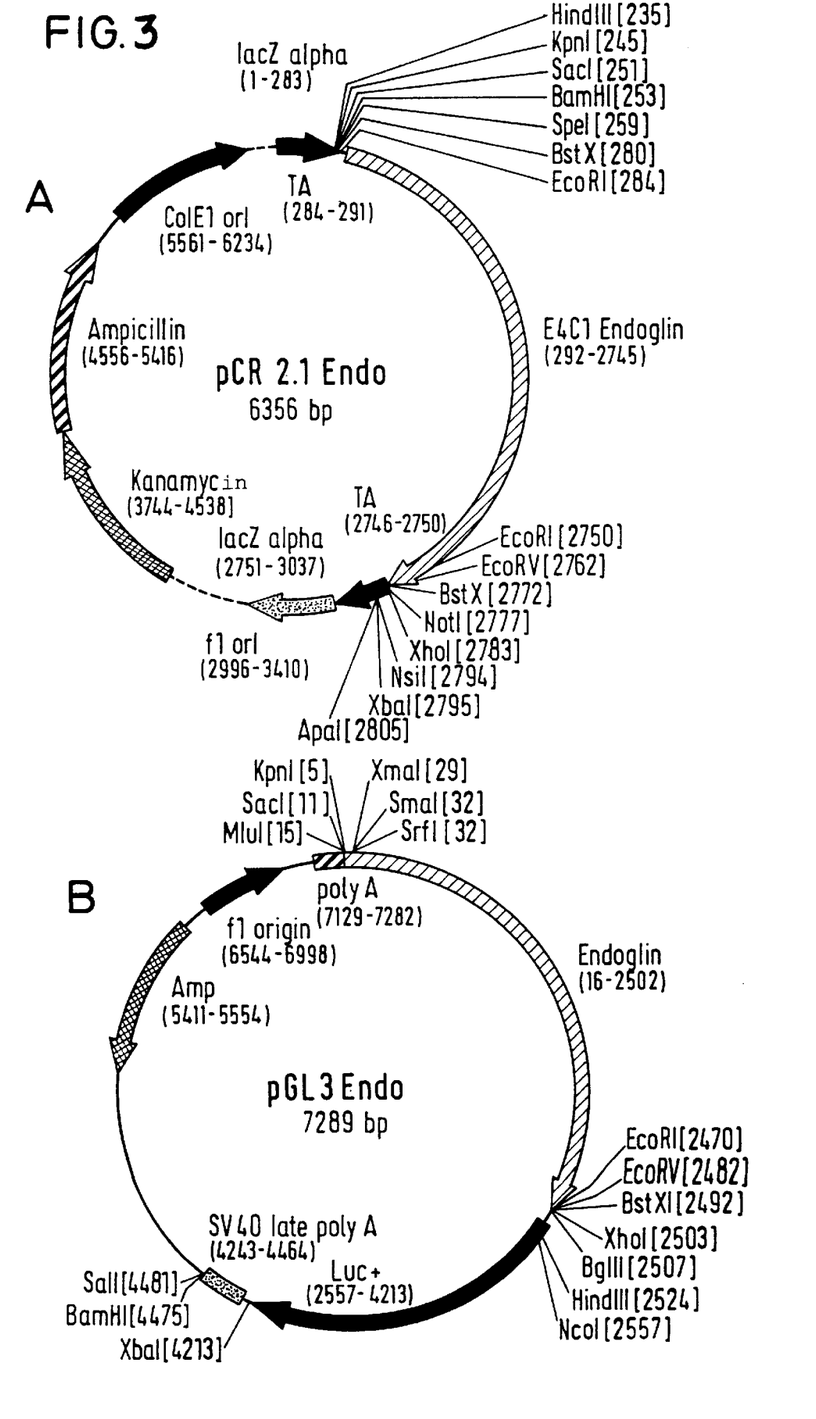
FIGS. 3A and 3B show details of the pCR 2.1 Endo and pGL3 Endo vectors. A is a fragment of the human endoglin promoter prepared by means of PCR and which was ligated into the TA cloning site of the vector pCR 2.1 (Invitrogen). B is a fragment containing the human endoglin promoter that was excised from the construct pCR 2.1 Endo with the enzymes Mlul and Xhol and cloned into luciferase reporter vector pGL3 (Promega).
Figure 4:
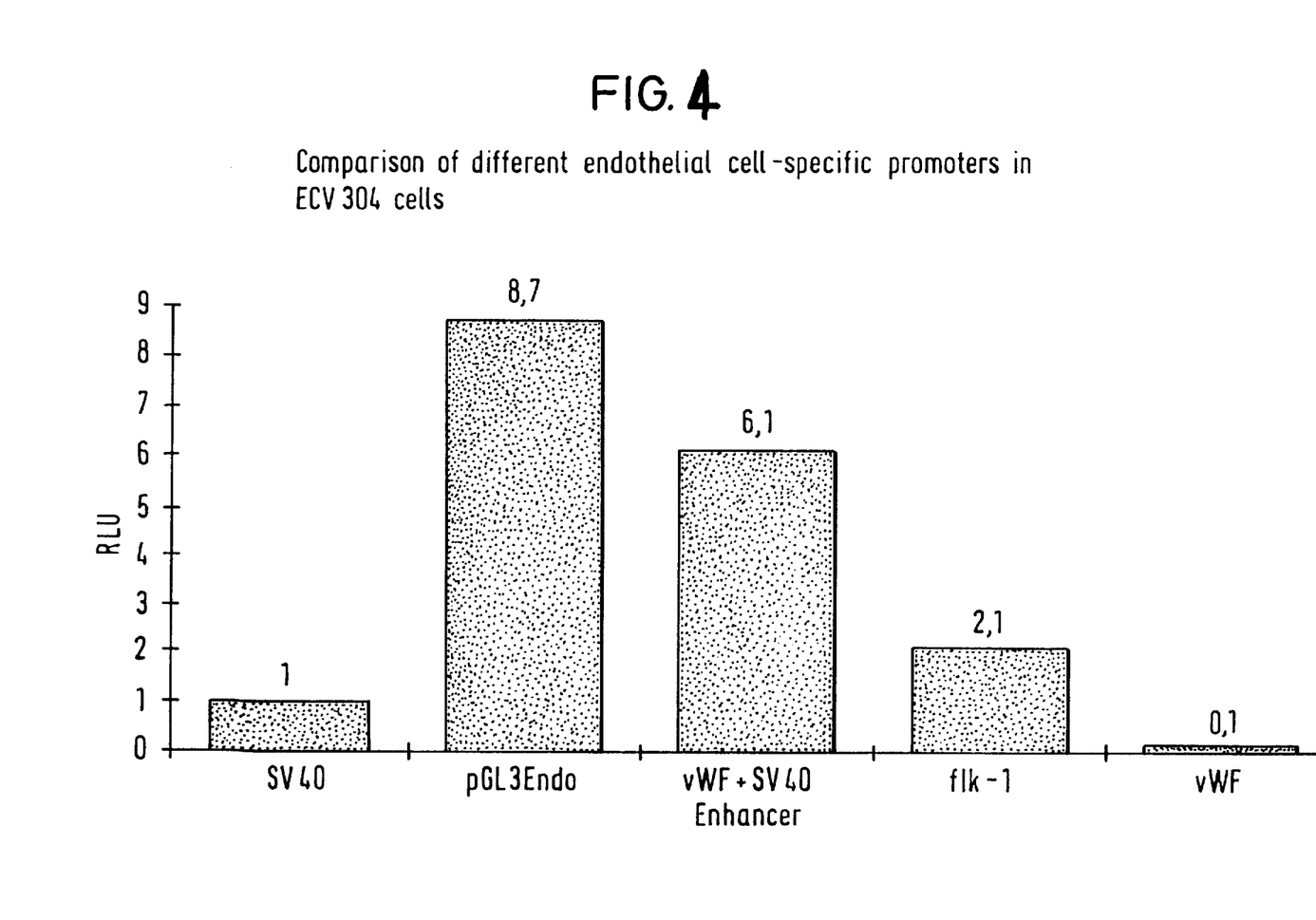
FIG. 4 depicts luciferase expression under the control of different endothelial cell-specific promoters. All of the promoters are cloned into pGL3 and all of the reported values are standardized on the SV40 basal promoter. SV40: SV40 basal promoter without enhancer. pGL3Endo: endoglin promoter (see FIG. 3B). vWF+SV40 enhancer: the von Willebrand factor promoter enhanced with an upstream SV40 enhancer. flk-1—the promoter for the VEGF receptor flk-1 (−224/starting ATG). vWF—the von Willebrand factor promoter (−487/+247) without additional enhancers.
Figure 5:
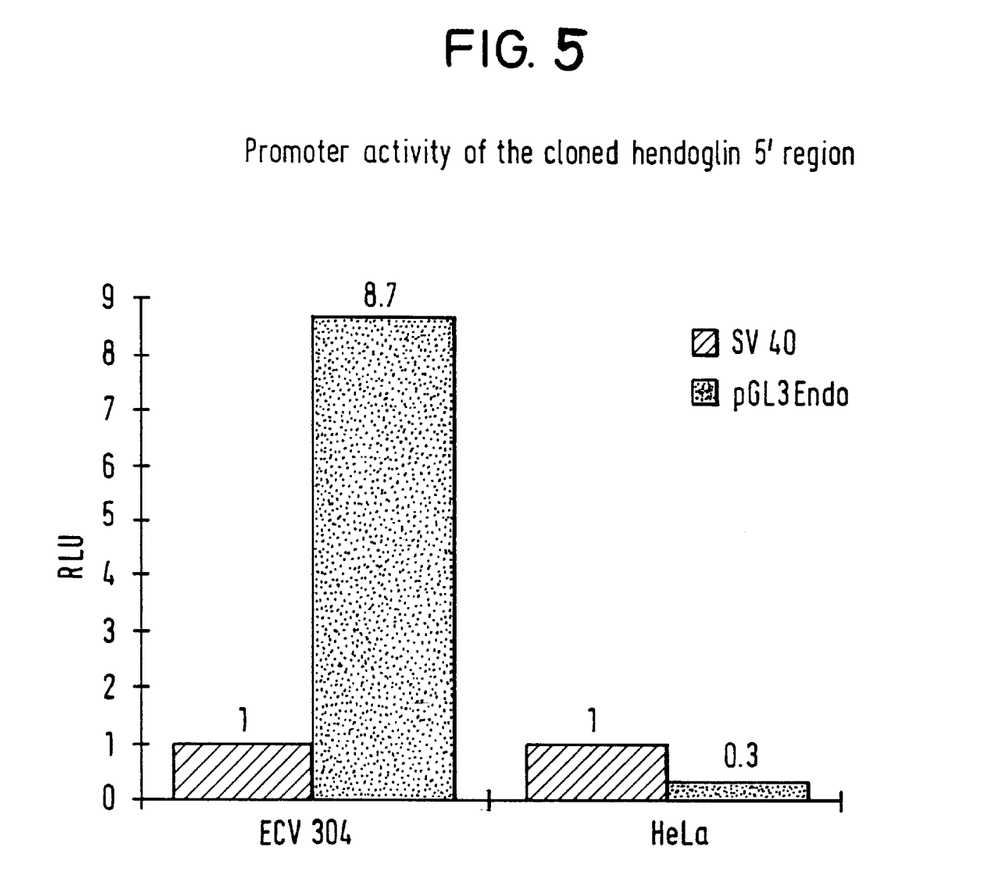
FIG. 5 contrasts, using luciferase expression, endoglin promoter activity in endothelial cells and non-endothelial cells. The constructs are the same as in FIG. 4 and standardized on the SV40 basal promoter. The activity of the endoglin promoter in the endothelial cell line ECV304 was compared with its activity in the HeLa cervical carcinoma cell line. In this assay, the activity in ECV304 cells is approximately 29 times higher than in HeLa cells. This indicates that the cloned promoter is not only active in endothelial cells but is also selective for these cells.
Figure 6:
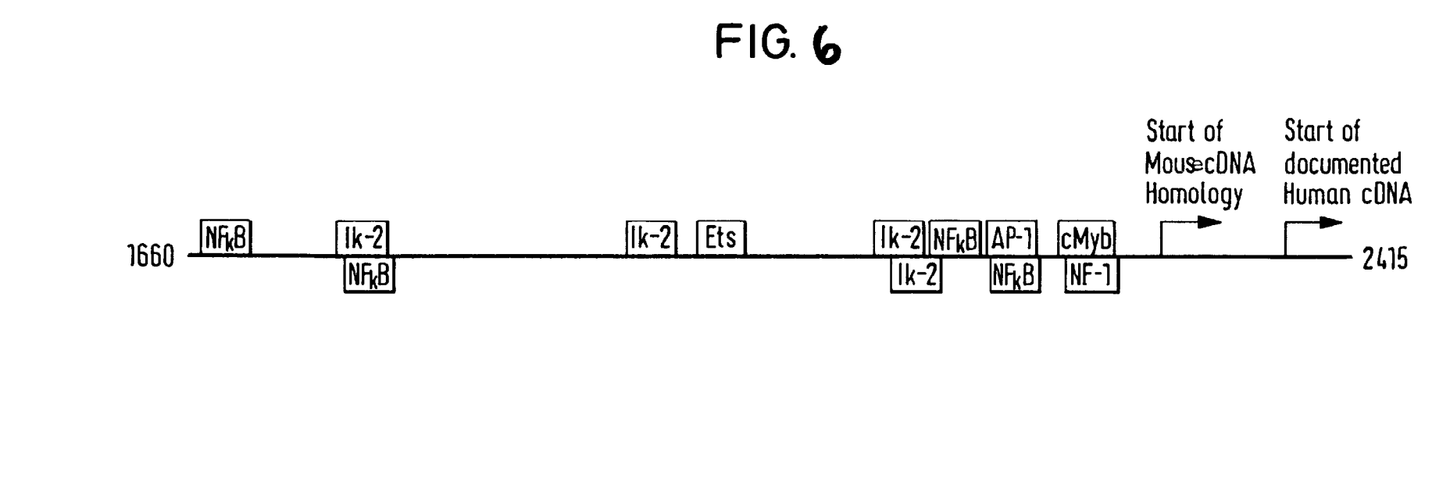
FIG. 6 shows putative binding sites for transcription factors on the endoglin promoter between the Alu sequence and the beginning of the cDNA. Only the region between the Alu sequence and the beginning of the CDNA is shown. All the binding sites are located on the plus(+) strand. Some strongly homologous potential binding sites, which could be responsible for the selectivity and activity of the promoter and which include several conserved NF-KB binding sites, are located in the region between a conserved Alu sequence and the documented CDNA.

The PCR fragment was purified through QlAquick (TM) spin columns (Qiagen) and inserted into a TA cloning vector (Original TA Cloning (TM) kit (Invitrogen)). This construct, pCR 2.1 Endo (see FIG. 3A), was sequenced and the cloned region was identified as a 2415 base pair 5' region of the human endoglin gene (see FIG. 2).

The cloned region from this vector was cloned into a luciferase reporter vector, i.e. pGL3 (Promega), and tested for its promoter activity, as the construct pGL3Endo (see FIG. 3b), in HeLa and ECV304 cells.

The cells were transfected either by the DEAE/dextran method (adapted from Sompayrac et al., PNAS 78, 7575 (1981)) or using LipofectAMINE TM (Gibco BRL). As well as the pGL3Endo construct, the SV40 basal promoter was transfected as a standard; the fik-1-(VEGF) (−225/starting ATG) promoter and also the von Willebrand factor (vWF) (−487/+247) promoter, with or without SV40 enhancer, were also transfected. This latter vWF promoter construct containing an SV40 enhancer is distinctive in that its activity is markedly higher than that of the wild-type promoter, while its selectivity, although reduced, is not abolished. All the constructs were cloned into pGL3, and the luciferase assay was performed as described in Herber et al. (Oncogene 9, 1295 (1994)) and Lucibello et al. (EMBO J. 14, 132 (1995)).

The luciferase activity of the different promoters in ECV304 cells (FIG. 2) demonstrates that the cloned fragment of the 5' region of the endoglin gene possesses a promoter activity. This activity is very high when compared with that of other typical endothelial cell-specific promoters. The activity is four times higher than that of the flk-1 promoter and more than eighty times higher than that of the vWF promoter. The activity of the pGL3Endo construct is higher even when the vWF promoter is enhanced with an SV40 enhancer sequence. These data confirm that the cloned region is the promoter of the human endoglin gene.

The publications and patents cited are herein incorporated in their entireties by reference. The priority application DE 19704301.1 is herein incorporated by reference.

We claim:

1. A promoter of the human endoglin gene, comprising a sequence selected from SEQ ID NO: 1 having promoter activity, or a partial sequence of the promoter which possesses promoter activity.

2. A promoter as claimed in claim 1, wherein said sequence comprises at least one sequence selected from the group consisting of approximately 1 to approximately 2378, from approximately 36 to approximately 2378, from approximately 470 to approximately 2378, from approximately 948 to approximately 2378, from approximately 1310 to approximately 2378, from approximately 1847 to approximately 2378, from approximately 36 to approximately 2415, from approximately 470 to approximately 2415, from approximately 948 to approximately 2415, from approximately 1310 to approximately 2415, and from approximately 1847 to approximately 2415, from the positions shown in FIG. 1.

3. A nucleic acid construct, comprising at least one promoter sequence of the human endoglin gene as claimed in claim 1.

4. A nucleic acid construct as claimed in claim 3, further comprising an effector gene, wherein said promoter sequence activates the transcription of said effector gene.

5. A nucleic acid construct as claimed in claim 4, wherein said promoter sequence is upstream of the effector gene.

6. A nucleic acid construct as claimed in claim 3, further comprising at least one additional activation sequence, wherein said activation sequence is selected from the group consisting of a virus-specific sequence, a metabolism-specific sequence, cell-specific sequence and a cell cycle-specific sequence.

7. A nucleic acid construct as claimed in claim 3 wherein said nucleic acid is DNA.

8. A vector comprising a promoter of the human endoglin gene, said promoter comprising a sequence selected from SEQ ID NO: 1 having promoter activity, or a partial sequence of the promoter which possesses promoter activity.

9. A vector as claimed in claim 8, wherein said vector is a plasmid or virus.

10. A nucleic acid construct as claimed in claim 4, wherein said effector gene encodes an active compound selected from the group consisting of a cytokine, a chemokine, a growth factor, a cytokine receptor, a chemokine receptor, a growth factor receptor, a cytokine antagonist, a protein having an antiproliferative, cytostatic or apoptotic effect, an antibody, an antibody fragment, an angiogenesis inhibitor, a coagulation factor, a coagulation inhibitor, a fibrinolytic protein, an enzyme which cleaves a precursor of a drug thereby forming a drug, a protein having an effect on the blood circulation, and an antigen of an infectious pathogen which evokes an immune reaction.

11. A nucleic acid construct as claimed in claim 3, comprising at least two effector genes, wherein said effector genes are linked to each other by at least one said promoter sequence or an internal ribosomal entry site sequence.

12. A host cell that comprises a nucleic acid construct as claimed in claim 3.

13. A composition comprising a nucleic acid that comprises a sequence selected from SEQ ID NO: 1 having promoter activity, or a partial sequence of the promoter which possesses promoter activity, in a carrier.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 2415 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:1:

```
CGGGGGTTCC TCCTCTGTAA AGTGGAGGTA TAACGGTACC CACCTCCTGG GGTGGCTGTG      60

AGGATTCAGA GCTGATAAGG TGAACGCCTA GGGCGGGCCC TGGTGCAGAG AGAGCGCTCA     120

GCTCCTAGGG CTGGATTAAC TGTCCCTGGG GCACAGATCT CGGTCTGGGG CCTGTGGAAA     180

CCTCAGAGCC ACCCCTGAAC CCCCACCGAG CCACCCTTTG CCTCGCAGTG CCCATGGCCT     240

CGTCTCCGAG GTTACAGGAA AAGGCAGAGG AGATGCCCTT CTCAGGGTGG CCCTCTGGGA     300

GAGGACACTC TCCCTTGACC TCAAAGCCAC GCTTGGCTGC AAACTGGCCA GGCAGCCACA     360

AGGCTGGGCA AGCAGAACGA TCCCTAATCC CCACCCAAAG AGCCACACCG ACCCTCCCAG     420

CCGCTGTGAC AGCTCCTGCA GAGACAAACA CACGGCCTAC TCTTGTCACC CGGGCCGGCC     480

AATAAGCACG GAGAGGCAAG GCCTCAGACC CTGGACAGAC ATCCTCCCTC CAGAGGCACC     540

AGGGCCTCAG CCTTCTCCTC CCTCCCTGGG CCTCAATTTC TCCACCTGTG ACCCAGGGCA     600

GGTGGATCCA GGGAGAAGAA CCTTCTGGCT CCATCTCACC ATGGGTCCTG CCAGCACACA     660

CAAAGATTTG GCCTCTCAAA GCCTAGCTCT GCCAGCGTCC TTCTGCTCAA GAACTCTCCA     720

TGACTCCCAG TGGCCCTAAG GACAAAGTCC TGGCATTTGA GGCCCTCCCA ATGCAGGGCC     780

AGACTCTGCC TCTCCAGCTT CCTGTCCCCA CCACACCCCT GCTGGTCTCA CGGTGGTCCG     840

ACTGTTTCCT GCTTCTGTGC CTTTGCTTAG TCTGGCACCC CTGCCTGGCA TGCTTTCCTC     900

ACCCCTTCTT CTCCCCAATC CCAACTCACC CAGTCTTTCA AAGGGCAGGC CTAAATACCA     960

GGCCCTCCAG GTGGCCCAGG ATTCCTTCTC TGAGCTTTCA TGGGCCTGGC CCTGGGTGCT    1020

ACCTGTGAGT AGTCCCACGG TGGGTACATA GTAGGTGCGC TTACTGTTCG CAGAATGAAC    1080

ATGGGACAGT TTGGGACTG TCACCCAGCT CAGGGAGCAC TGATGGGAA GCATCTCCTG      1140

TATGTCCCAG GGCTCAGTGC TGTAGTGTCC TGACCCTCAG AAATCTCATA ATGGCTTGGT    1200

CAGGAAGGCA TCGTGCCCCA CTTTGCAAAC AGGGGGTGCT GAGAATTGAG GGGCCTTGTC    1260

CAAGGTCTCA TGGCTAGGAG CAAGCAGAAT CGGATTTGAA CCCAGGGCCA CGTGACTTCA    1320

GAAGTGCCAT TAAAGTCCCC ATAATTCGGA GCTGTCTTCT TTTTTTTTTT CTTTCTTTTT    1380

TTTGAGACCG AGCCTCACTC TGTCACCTAG GCCAGGAGTG CAGTGGTCTG ATCTCAGCTC    1440

ACTGCAACCT CCGCCTCCTA GGTTCAAGTG ATTCTCTAGC CTCAGCCTCC CAAGTAGCTG    1500

GGACTACAGG CGCACGTCAT CATGCCCAGC TAACTTTTGT ATTTTTAGTA GAGATGGGTT    1560

TTCACCATGT TGGTCAGGCT GGTCTCGAAC TCCTGACCTC AAGTGATCCG TCTGCCTCGG    1620

CCTCTCAAAG TGCTGGGATT ATAGGCTTGA GCCACTACAC TCGGCCTGGA GCTGTGTTTT    1680

GTCGGTGAAG GATTTTCCAC CCATGAAGGG GTCAGACGTG AAGCGTGTGG CCCTGGGCAG    1740

CTCCTCTGAG CCCAGAGACG CCAGCCCTAG CCGCCTTGCT GTGCCACTTT GGGACTTCCC    1800
```

```
TCCCTAGCCT GAGCTTCAGT TTTCCTGCCT GTTAGGCAGC CCCATGTCAA CTGCACTTAG    1860

TAGGCCGGGT TTGATGCCCG ACAAGACGTG AAGTGGTGGA GGTGGGCAGG ATCCCAGCGC    1920

TACCATCTTC TTGAACCAGT GATCTCAACA CATCGGATTT CTGTTTCCTC ATCTGCAAAA    1980

TGGGATCAGT GAGCTCAGGT GGGTCACAAA TTCTACAGGA ACTACTTTAG CCAAGCCCGG    2040

CCCCCTGAAA GTTCCCCTCG GTGGGCAGTT AGGGTGATTG TTTTCATCTG TGGGGCTCCC    2100

TGATGCGTCC CACCCACCAG CCTTGGAGAG GGTGGGATGG GAGGGTGGGG TGCTTGGGGA    2160

GACAAGCCTA GAGCCTGGGC CCTCCCACCC CACTGCCTCC CCCCATCCCA GGGCCCCCCA    2220

CCCAGTGACA AAGCCCGTGG CACTTCCTCT ACCCGGTTGG CAGGCGGCCT GGCCCAGCCC    2280

CTTCTCTAAG GAAGCGCATT TCCTGCCTCC CTGGGCCGGC CGGGCTGGAT GAGCCGGGAG    2340

CTCCCTGCTG CCGGTCATAC CACAGCCTTC ATCTGCGCCC TGGGGCCAGG ACTGCTGCTG    2400

TCACTGCCAT CCATT                                                    2415

(2) INFORMATION FOR SEQ ID NO:2:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GCTGGGCTGG AGTTGCTGTC CGAAGGATG                                      29

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

AATGGATGGC AGTGACAGCA GCAGTCCTG                                      29
```